United States Patent [19]

Patel

[11] Patent Number: 5,465,735
[45] Date of Patent: Nov. 14, 1995

[54] WOUND DRESSING

[75] Inventor: Harish A. Patel, Norfolk, Mass.

[73] Assignee: The Kendall Company, Mansfield, Mass.

[21] Appl. No.: 347,661

[22] Filed: Dec. 1, 1994

[51] Int. Cl.$^6$ ................................. A61F 13/00
[52] U.S. Cl. ................... 128/888; 602/41; 602/47; 602/56
[58] Field of Search .................... 128/846, 888; 602/41, 42, 43, 46, 47, 52, 54, 56, 58, 59

[56] References Cited

U.S. PATENT DOCUMENTS

| | | | |
|---|---|---|---|
| 2,923,298 | 2/1960 | Dockstader | 602/47 |
| 3,285,245 | 11/1966 | Eldredge | 602/56 |
| 4,341,207 | 7/1982 | Steer | 602/56 |
| 5,060,642 | 10/1991 | Gilman | 602/56 |
| 5,244,457 | 9/1993 | Karami | 602/55 |

Primary Examiner—Michael A. Brown
Attorney, Agent, or Firm—David J. Koris

[57] ABSTRACT

Disclosed are wound dressings comprising an absorbent pad for receiving and retaining wound fluids sandwiched between first and second outer sheet materials, the first sheet material for placement on the wound being a perforated non-adherent film for preventing the dressing from sticking to the wound, the second sheet material being characterized as being bacteria-impermeable, the absorbent pad being a multilayer structure comprising an inner layer of a low density absorbent material for receiving fluids diffusing to the dressing from the wound and an overlying layer of a high density absorbent material for receiving and retaining wound fluids diffusing through the inner layer in order to inhibit skin maceration due to the wetness of the surface area of the absorbent pad adjacent the wound.

6 Claims, 2 Drawing Sheets

WOUND DRESSING

BACKGROUND OF THE INVENTION

As is well recognized in the art, ideally a wound dressing comprising an absorbent material providing a reservoir for the wound fluids diffusing from the wound should not interfere with normal wound healing. Yet, where the dressing comprises an absorbent pad of a fibrous material such as gauze which is in immediate contact with the wound, the diffusing wound fluid will extend into the interstices and around the fibers of the dressing so that the dressing is eventually adhesively and mechanically anchored into the wound surface, e.g. to graft sites, buds of new tissue forming over the wound or to the scabby protective covering for the wound.

Consequently, removal or changing of the dressing can and will cause disruption of the healing process, delaying the healing process as well as being a painful procedure for the patient.

For these reasons, wound dressings have been well known and have received wide commercial acceptance wherein the absorbent material is sandwiched between outer perforated non-adherent films preventing the dressing from sticking to the wound, being described, for example, in U.S. Pat. No. 2,923,298.

As an example of such commercial dressings, mention may be made of the TELFA® adhesive dressings and pads and the TELFA® adhesive island dressings commercially available from the Kendall Healthcare Products Company, a division of The Kendall Company, assignee of the present invention.

While they are highly efficacious in that they provide the desired protective absorbent dressing while preventing adherence to the wound, they nevertheless tend to cause skin maceration if the dressing is not changed once it becomes saturated with wound fluid. Additionally, the pooling of wound fluid on the wound surface once the dressing becomes saturated tends to diffuse laterally to undermine the adhesive outside the wound area holding the dressing to the skin.

Wound dressings are also well known in the art where a bacterial-impermeable cover sheet is provided over the absorbent fabric material to provide an aseptic environment to inhibit or preclude infection of the healing wound. Preferably the bacteria-impermeable cover is also oxygen-permeable to permit release of air within the interstices of the fabric material in order to maximize the efficiency of the absorbent fabric for receiving and retaining wound fluid before a dressing change is required. Suitable materials of this description are well known in the art and include, for example, polyurethane, a polyolefin such as polyethylene or polypropylene, "Saran" (trademark of Dow Chemical), a polyester such as polyethylene terephthalate, etc. The concept of providing a cover sheet which is oxygen-permeable, bacteria-impermeable is disclosed, for example, in U.S. Pat. Nos. 5,056,510, 5,167,613, 5,244,457 and 5,308,313 all assigned to The Kendall Company.

Stated simply, the task of the present invention is to provide a non-adherent wound dressing which obviates the above-noted problem of maceration due to pooling of wound fluid and which, additionally, can provide an environment covering the wound which can prevent ingress of bacteria.

BRIEF DESCRIPTION OF THE INVENTION

In accordance with this invention, the task is solved in an elegant and expeditious manner by providing a wound dressing having a multilayer absorbent material comprising a first or lower layer of a low density absorbent fiber exhibiting optimum absorption capacity and a second or upper layer of a high density absorbent fiber having optimum spreading or wicking characteristics; the multilayer absorbent material being sandwiched between upper and lower sheet materials, the lower sheet material adapted for placement on the wound being a perforated, non-adherent sheet material of the type known in the art such as those mentioned above, the upper sheet material covering the dressing being a bacteria barrier, such as known in the art, and preferably also being oxygen-permeable.

In the preferred embodiment, the dressing is an island dressing.

DETAILED DESCRIPTION OF THE INVENTION

As heretofore mentioned, the present invention is directed to improvements in non-adherent film dressings.

The nature and objects f the invention will best be understood by reference to the following detailed description taken in conjunction with the accompanying drawings illustrating the preferred embodiments of the invention.

Figure 1:
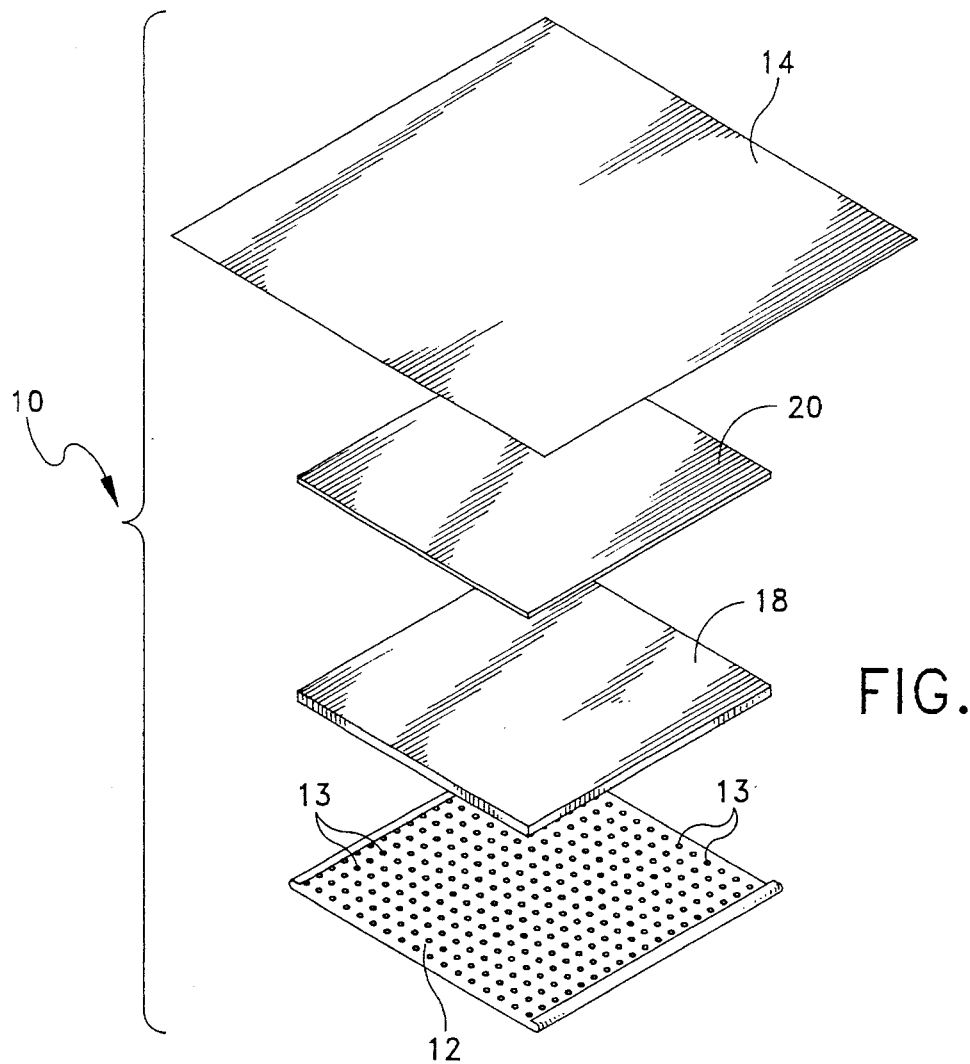
FIG. 1 is an exploded view showing the essential elements of one embodiment of the invention.
Figure 2:
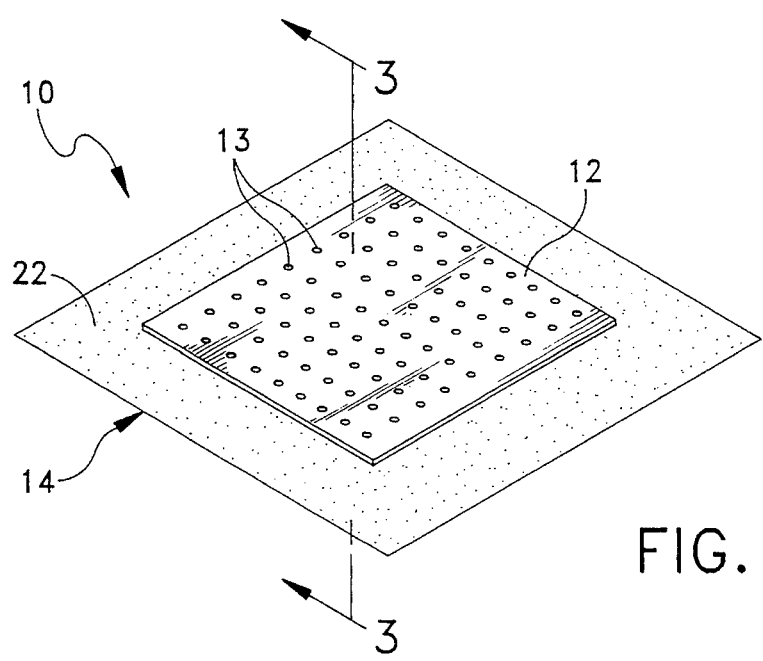
FIG. 2 is a perspective view of the side of the dressing to be applied to cover a wound.
Figure 3:
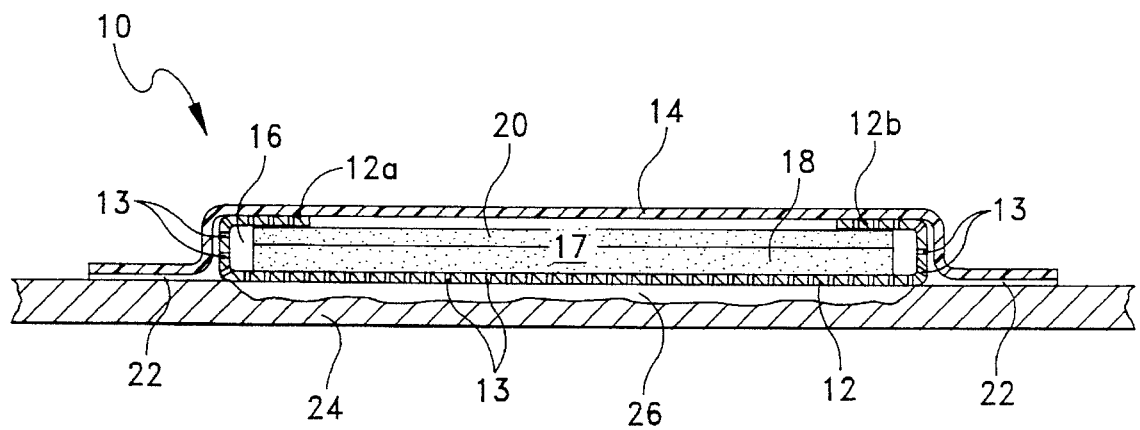
FIG. 3 is a sectional view taken along line 3—3 of FIG. 2.

FIGS. 1–3 relate to an island dressing in accordance with this invention. As shown therein, dressing (10) has sheets (12) (14) defining a chamber (16) in which is disposed an absorbent pad (17) for receiving and retaining wound fluids diffusing from the wound.

In accordance with this invention sheet (12), adapted for placement on the wound, is a non-adhering perforated sheet material permitting wound fluids to diffuse therethrough to the absorbent pad (17); while sheet (14) provides a bacterial barrier, preventing ingress of ambient bacterial into the dressing where the bacteria can then contaminate the wound and cause infection.

Absorbent pad (17) is of a multilayer configuration which, in the embodiment shown in FIG. 3, consists of two contiguous absorbent layers (18) and (20), layer (18) being a low density absorbent material and layer (20) being a high density absorbent material, as will be described in detail hereinafter. As seen in FIG. 3, perforated sheet 12 (12) is wrapped around the edges of the absorbent pad (17) with its edges 12(a) (12b) overlapping the upper surface of the absorbent pad.

As seen in FIG. 2, sheet (14) has a layer of pressure-sensitive adhesive (22) on its inner surface, that is, the surface facing perforated sheet (12). The absorbent pad (17), which is of substantially smaller dimensions than sheet (14), is substantially centrally seated on the adhesive surface (22) of sheet (14), thereby securing pad (17) and the edges (12a) (12b) of sheet (12) to sheet (14), thus providing an island dressing adapted for securing the dressing (10) to the skin

(24) of a patient surrounding a wound (26).

The differences between the dressing shown in FIGS. 1–3 and described above and island dressing such as the TELFA® adhesive island dressing sold for many years by the present assignee, which differences are the essence of the improvement upon which patentable novelty is here predicated, are two-fold: (1) the concept of providing, for the absorbent pad what may be said to be a two-layer pad structure with the inner layer to be positioned closest to the wound surface being of a low density material, the upper layer superposed thereover being of a high density material, and (2) the concept of providing a bacteria-impermeable cover or outer sheet over the reservoir (16) containing the absorbent pad (17).

The concept of providing a wound dressing having a low density/high density absorbent pad structure is per se old, being disclosed, for example, in U.S. Pat. Nos. 5,167,613 and 5,244,456 issued to Karami et al and assigned to the assignee of the present invention.

As described therein, while the reservoir for receiving wound fluids in the described dressings may comprise any of the fabric materials heretofore employed to retain exudate, e.g. cotton, gauze sponges, absorbent pads such as those customarily used for abdominal surgery, and the like, they will most preferably consist of two separate but contiguous elements, namely a lower high density woven or non-woven fabric having optimum spreading or wicking characteristics and an upper low density fabric having optimum absorption capacity. Preferably, the high density fabric will have a density of on the order of 0.1 to 0.2 gms/(cm)$^3$; while the low density fabric will have a density less than 0.1 gm/(cm)$^3$, e.g. on the order of 0.05 gm/(cm)$^3$. The combination of the two fabrics will typically provide a weight per surface area of on the order of 7 ounces/square yard, the ratio of low: high density by thickness being on the order of about 3:1 to about 5:1. The fabrics may be woven or non-woven materials, non-woven being preferred, and illustrative fibers include rayon, rayon/polyester or polyester/cotton blends, cotton, cellulosic materials, etc.

In the wound dressing which is the subject matter to which the aforementioned patents are directed, the purpose of having high density fabric nearest the wound is to provide optimum spreading or wicking characteristics in order to facilitate exudate being absorbed over substantially the entire surface area of the absorbent fabric; while the upper or overlying low density woven or non-woven fabric possesses optimum absorption capacity, the composite absorbing fabric thereby providing maximum efficiency of the fabric for absorbing wound exudate before become saturated so as to require a dressing change.

While the present invention employs the same materials as described above, it will be seen that the task is different and accordingly the order of the two fabrics is reversed so that the low density fabric for optimum absorption is nearest the wound, thereby distinguishing over the teaching of the aforementioned patents.

As heretofore mentioned, the concept of providing a cover sheet for a wound dressing which is bacteria-impermeable and oxygen-permeable, i.e. prevents ingress of bacteria while permitting egress of entrained air, is per se old and described, for example, in the patents mentioned in the BACKGROUND OF THE INVENTION. Sheet (14) may accordingly be any of the known films which are bacteria-impermeable but preferably oxygen-permeable.

In the island dressing shown in FIG. 3, it will be appreciated that sheet (14) in combination with adhesive 22 securing the dressing to the skin (24) surrounding a wound (26) provide a chamber surrounding the wound which is a barrier against ingress of bacteria.

Figure 4:
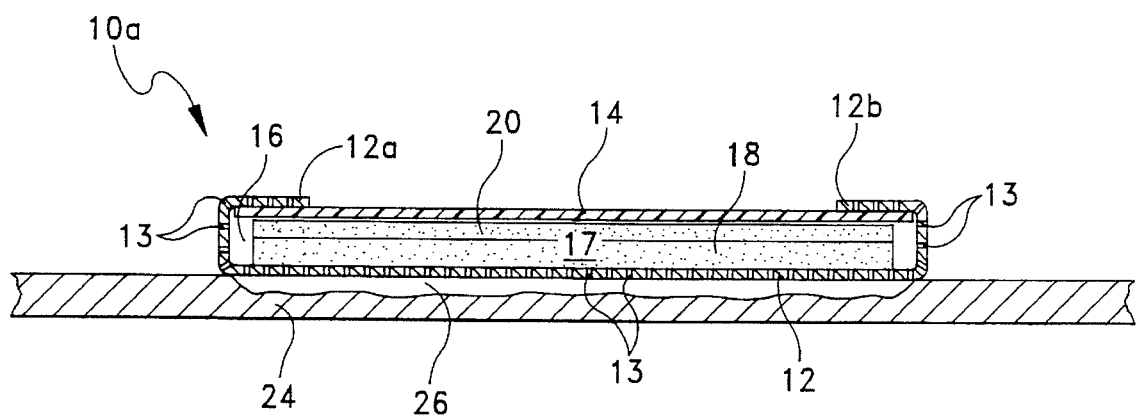
FIG. 4 is a view similar to FIG. 3 showing another embodiment of this invention.

FIG. 4 relates to an alternate embodiment of the invention wherein, unlike the island dressing of FIGS. 1–3, the dressing (10a) does not itself contain a free adhesive surface to adhere the dressing to the skin. Instead, as shown, perforate sheet (12) is somewhat larger than bacteria-impermeable sheet (14), with it free edges (12a) (12b) extending over sheet (14) and being secured thereto, e.g. by heat sealing or by adhesive means such as a pressure-sensitive adhesive, in order to enclose the reservoir (16) containing the absorptive pad (17).

As will be appreciated, the wound dressing (10a) of FIG. 4 may be secured to the skin by means of adhesive tape strips. It will also be appreciated that if an aseptic, bacteria-free environment is to be maintained, the tape securing the bandage to the skin and/or other means should be provided to cover the exposed lateral perforations (13) on the edges of the bandages.

Figure 5:
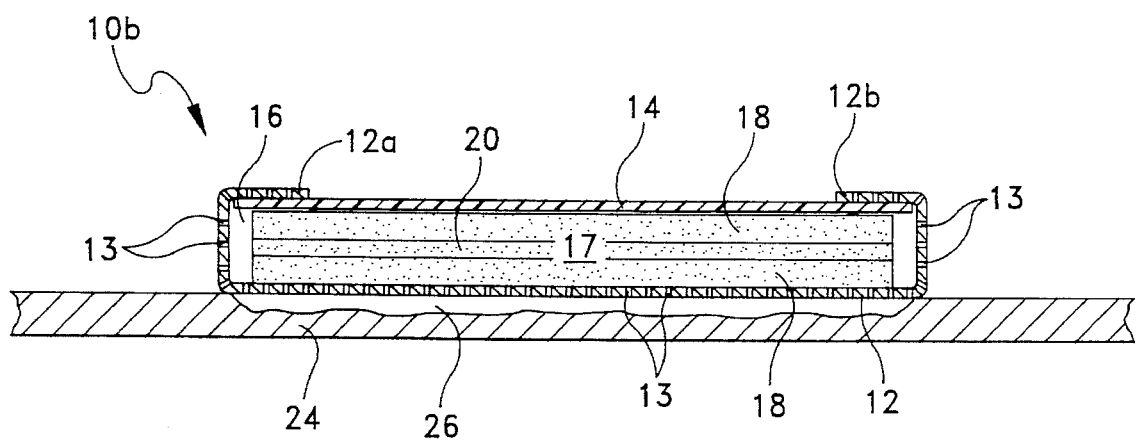
FIG. 5 is also a view similar to FIG. 3 of still another embodiment of this invention.

FIG. 5 relates to another embodiment in which the dressing (10b) is similar to the dressing (10a) of FIG. 4, the distinction being that dressing (10b) is symmetrical in that it contains an outer layer of low density fabric (18) so that the absorptive pad (17) consists of a layer of a high density fabric (20) sandwiched between outer layers (18) of low density fabric.

As was heretofore mentioned, the materials to be employed for sheets (12) (14) are per se old and well known in the art. Accordingly, their selection comprises no part of this invention, but will be a matter of individual choice within the expected judgment of the skilled worker in the light of this description.

By way of illustration, perforated sheet (12) should be relatively thin, e.g. on the order of 10 mil or less, should possess a high degree of conformability and, of course, be non-toxic or in any way delay wound healing. The perforations (13) in the films should be sufficient to permit wound exudate to diffuse through the film at a rate which precludes pooling on the wound to cause maceration. For example, there may be on the order of 370–390 perforations per square inch having a diameter on the order of 0.020–0.040 inch. As was stated, suitable materials for sheet (12) include polyesters, polyolefins and the like polymeric materials.

Non-perforated bacteria-impermeable sheet (14) should also be relatively thin and be highly conformable. It may, for example, be on the order of 0.5 to 2.0 mil thick.

The adhesive to be employed for layer (22) may be any of the so-called medical grade or hypoallergenic pressure-sensitive adhesives heretofore employed for wound dressings and medical tapes. Such known adhesives include the rubber-based, acrylic, vinyl ether and hydrocolloid pressure-sensitive adhesives. The adhesive (22) may be coated to provide a layer at least 1 mil thick, preferably at least 5 mils thick.

While not an essential part of the invention, it will be appreciated that the island dressing (10) should also have a standard release sheet covering the free adhesive layer (22) in order to prevent premature and unwanted adherence of the adhesive to a substrate.

Since certain changes may be made without departing from the scope of the invention herein contemplated, it is intended that all matter contained in the foregoing description, including the accompanying drawings, shall be taken as being illustrative and not in a limiting sense.

What is claimed is:

1. A wound dressing comprising an absorbent material for receiving and retaining wound fluids sandwiched between opposed first and second outer sheet materials, the first sheet material for placement over a wound being a perforated non-adherent film for preventing the dressing from sticking to the wound;

the second sheet material being characterized as being bacteria-impermeable;

the absorbent material being a multilayer structure comprising first and second absorbent layers, the first layer being a low density absorbent fabric having optimum absorption capacity for receiving wound fluids diffusing from the wound through the first sheet material, the second layer being a high density absorbent fabric exhibiting optimum spreading or wicking characteristics for receiving and retaining wound fluid diffusing through the low density absorbent fabric, whereby to inhibit maceration caused by pooling of wound fluid on the wound surface.

2. A wound dressing as defined in claim 1 wherein the dressing is an island dressing.

3. A wound dressing as defined in claim 1 wherein the low density fabric has a density less than 0.1 gram per cubic centimeter and the high density fabric has a density on the order of 0.1 to 0.2 gram per cubic centimeter.

4. A wound dressing as defined in claim 1 wherein the second sheet material is further characterized as being oxygen-permeable.

5. A wound dressing as defined in claim 3 wherein the second sheet material is further characterized as being oxygen-permeable.

6. A wound dressing as defined in claim 1 wherein the absorbent material contains a third absorbent layer disposed on the outer surface of the second absorbent layer, the third absorbent layer being a low density absorbent fabric, whereby the absorbent material consists of a high density absorbent fabric sandwiched between outer layers of a low density absorbent fabric.

* * * * *